US011692918B2

United States Patent
Peng et al.

(10) Patent No.: US 11,692,918 B2
(45) Date of Patent: Jul. 4, 2023

(54) PRESSURE-PRESERVING CONVENTIONAL TRIAXIAL COMPRESSION LOADING APPARATUS AND METHOD FOR PERFORMING CONVENTIONAL TRIAXIAL COMPRESSION TEST ON PRESSURE-PRESERVING SPECIMEN USING SAME

(71) Applicant: CHINA UNIVERSITY OF MINING AND TECHNOLOGY, BEIJING, Beijing (CN)

(72) Inventors: Ruidong Peng, Beijing (CN); Hongwei Zhou, Beijing (CN); Wenhao Jia, Beijing (CN); Yu Yang, Beijing (CN); Kai Si, Beijing (CN); Jianqiang Wang, Beijing (CN)

(73) Assignee: CHINA UNIVERSITY OF MINING AND TECHNOLOGY, BEIJING, Beijing (CN)

( * ) Notice: Subject to any disclaimer, the term of this patent is extended or adjusted under 35 U.S.C. 154(b) by 0 days.

(21) Appl. No.: 17/828,860

(22) Filed: May 31, 2022

(65) Prior Publication Data

US 2022/0381661 A1    Dec. 1, 2022

Related U.S. Application Data

(63) Continuation of application No. PCT/CN2021/097595, filed on Jun. 1, 2021.

(51) Int. Cl.
*G01N 3/10* (2006.01)
*G01N 3/06* (2006.01)
(Continued)

(52) U.S. Cl.
CPC ............... *G01N 3/10* (2013.01); *G01N 3/066* (2013.01); *G01N 33/24* (2013.01); *G01N 29/14* (2013.01);
(Continued)

(58) Field of Classification Search
CPC G01N 3/10; G01N 3/066; G01N 3/12; G01N 33/24; G01N 2203/0019;
(Continued)

(56) References Cited

U.S. PATENT DOCUMENTS

2022/0196527 A1*   6/2022   Liu ................. G01N 33/24

FOREIGN PATENT DOCUMENTS

| CN | 101182856 A | 5/2008 |
| CN | 205404294 U | 7/2016 |

(Continued)

OTHER PUBLICATIONS

International Search Report (PCT/ISA/210) in corresponding international application PCT/CN2021/097595, 5 pages.

*Primary Examiner* — Jonathan M Dunlap
(74) *Attorney, Agent, or Firm* — Muncy, Geissler, Olds & Lowe, P.C.

(57) ABSTRACT

A pressure-preserving conventional triaxial compression loading apparatus of the present invention includes a pressure vessel, an upper piston rod, a lower piston rod, and an annular oil bag assembly. Hollow chambers of the pressure vessel in vertical communication sequentially include an upper chamber, an upper sealed chamber, a confining pressure chamber, a lower sealed chamber, and a lower chamber from top to bottom. The annular oil bag assembly is placed in the confining pressure chamber. When an annular inner chamber of an annular oil bag is filled with medium, an outer wall of the annular oil bag and an inner wall of the confining pressure chamber are attached together. A fidelity specimen (Continued)

is placed in a specimen chamber defined by a lower end surface of the upper piston rod, an upper end surface of the lower piston rod, and an inner wall of the annular oil bag. A variety of measuring sensors are disposed in the annular inner chamber of the annular oil bag. The pressure-preserving conventional triaxial compression loading apparatus of the present invention may accommodate a fidelity specimen, and use the annular oil bag assembly and the upper and lower piston rods to perform a pressure-preserving conventional triaxial loading test on the fidelity specimen, so that test data is more accurate and reliable, to help to study the mechanical behavior of in-situ rock and measure their properties more faithfully.

9 Claims, 9 Drawing Sheets

(51) Int. Cl.
  *G01N 33/24* (2006.01)
  *G01N 29/24* (2006.01)
  *G01N 29/14* (2006.01)

(52) U.S. Cl.
  CPC ..... *G01N 29/24* (2013.01); *G01N 2203/0019* (2013.01); *G01N 2203/0048* (2013.01); *G01N 2203/0256* (2013.01)

(58) Field of Classification Search
  CPC ... G01N 2203/0048; G01N 2203/0256; G01N 29/14; G01N 29/24
  See application file for complete search history.

(56) References Cited

FOREIGN PATENT DOCUMENTS

| | | |
|---|---|---|
| CN | 108131355 A | 6/2018 |
| CN | 207848094 U | 9/2018 |
| DE | 102013205807 A1 | 10/2014 |
| EP | 2981458 | 2/2016 |
| ES | 2766929 T3 | 6/2020 |
| WO | WO2014161769 A1 | 10/2014 |

\* cited by examiner

PRESSURE-PRESERVING CONVENTIONAL TRIAXIAL COMPRESSION LOADING APPARATUS AND METHOD FOR PERFORMING CONVENTIONAL TRIAXIAL COMPRESSION TEST ON PRESSURE-PRESERVING SPECIMEN USING SAME

CROSS REFERENCE TO RELATED APPLICATIONS

This application is a Continuation of Application No. PCT/CN2021/097595, filed on Jun. 1, 2021, for which priority is claimed under 35 U.S.C. § 120, the entire contents of which are hereby incorporated by reference.

TECHNICAL FIELD

The present invention relates to a test loading apparatus, and in particular, to a loading apparatus used for a conventional triaxial compression test of rock under the condition of preserving pressure.

BACKGROUND

A conventional triaxial compression test of rock is an important method for studying the mechanical behavior of rock and measuring the mechanical properties of rock. For current conventional triaxial testers, a rock specimen obtained after sampling and cutting is placed in a confining pressure chamber of the tester, the rock specimen is wrapped with a rubber sleeve, a heat-shrinkable tube or silica gel, and then hydraulic oil is injected into the chamber for tests at different confining pressures. The rock specimen measured under such conditions basically has no pore pressure in an initial state, which is inconsistent with an actual rock state in the subsurface. Even if a pore pressure can be recovered through a seepage pressure, the rock specimen has been irreversibly changed during the variation of pore pressure, and the mechanical behavior of the rock specimen has been greatly affected.

A fidelity core with the original pore pressure and temperature can be obtained from underground rock formations by using an in-situ condition preserved coring technology, which has been applied in fields such as combustible ice coring and mine tunnel coring. However, since the obtained fidelity core is usually placed in a tank filled with a certain pressure-preserving medium, current conventional triaxial testers cannot realize a loading test on these fidelity cores under the condition of preserving pressure. Mechanical tests of the fidelity cores are facing huge challenges. It is necessary to develop a triaxial tester that can accommodate a fidelity core and can perform a conventional triaxial loading test on the fidelity core in an in-situ condition preserved environment to obtain more accurate test data.

SUMMARY

A technical problem to be resolved by the present invention is to provide a pressure-preserving conventional triaxial compression loading apparatus that can accommodate a fidelity core and can perform a conventional triaxial loading test on the fidelity core in an in-situ condition preserved state.

A pressure-preserving conventional triaxial compression loading apparatus of the present invention includes a pressure vessel, an upper piston rod, a lower piston rod, and an annular oil bag assembly, where the pressure vessel is formed by sealed connection of an upper cylinder block and a lower cylinder block, an upper annular boss is disposed on the upper piston rod, an annular area of the upper annular boss is equal to a cross-sectional area of the upper piston rod, a lower annular boss is disposed on the lower piston rod, an annular area of the lower annular boss is equal to a cross-sectional area of the lower piston rod, hollow chambers of the pressure vessel in vertical communication sequentially include an upper chamber, an upper sealed chamber, a confining pressure chamber, a lower sealed chamber, and a lower chamber from top to bottom, an upper cylinder cover is fixedly sealed on an upper end surface of the upper cylinder block, the upper annular boss fits the upper chamber in a sealed manner, the upper piston rod located below the upper annular boss fits the upper sealed chamber in a sealed manner, the upper piston rod located above the upper annular boss passes upward through the upper cylinder cover to fit the upper cylinder cover in a sealed manner, the upper annular boss of the upper piston rod divides the upper chamber into two chambers independent of each other, the two chambers are an upper balance chamber located above the upper annular boss and an upper compensation chamber located below the upper annular boss, a lower port of the lower chamber of the lower cylinder block is provided with a lower sealing assembly fitting the lower port in a sealed manner, a lower cylinder cover is fixed on a lower end surface of the lower cylinder block, the lower piston rod located above the lower annular boss fits the lower sealed chamber in a sealed manner, the lower annular boss fits the lower chamber in a sealed manner, the lower piston rod located below the lower annular boss sequentially passes downward through an inner hole of the lower sealing assembly and the lower cylinder cover, the lower piston rod fits the inner hole of the lower sealing assembly in a sealed manner, the lower annular boss of the lower piston rod divides the lower chamber into two chambers independent of each other, the two chambers are a lower balance chamber located below the lower annular boss and a lower compensation chamber located above the lower annular boss, the annular oil bag assembly is placed in the confining pressure chamber, the annular oil bag assembly includes an oil bag support and an annular oil bag fixed in the oil bag support, the oil bag support is inserted in a concave groove that is in an inner wall of the confining pressure chamber and fits the oil bag support, when an annular inner chamber of the annular oil bag is filled with a medium, an outer wall of the annular oil bag and the inner wall of the confining pressure chamber are attached together, a fidelity specimen is placed in a specimen chamber defined by a lower end surface of the upper piston rod, an upper end surface of the lower piston rod, and an inner wall of the annular oil bag, a variety of measuring sensors are disposed in the annular inner chamber of the annular oil bag, and the annular inner chamber, the specimen chamber, the upper balance chamber, the upper compensation chamber, the lower balance chamber, and the lower compensation chamber are chambers independent of each other and are separately provided with independent inlet and outlet pipes.

In the pressure-preserving conventional triaxial compression loading apparatus of the present invention, the oil bag support includes an upper annular body, a lower annular body, and several connecting rods, each connecting rod is a C-shaped body protruding outward, an upper end of the connecting rod is connected to an outer side surface of the upper annular body, a lower end of the connecting rod is connected to an outer side surface of the lower annular body, the upper annular body, the lower annular body, and the connecting rods are separately inserted in concave grooves that are in the inner wall of the confining pressure chamber and respectively fit the upper annular body, the lower annular body, and the connecting rods, end surfaces and inner side surfaces of the upper annular body and the lower annular body fit the concave grooves in the inner wall of the confining pressure chamber in a sealed manner, and the outer side surfaces of the upper annular body and the lower annular body and outer side surfaces of the connecting rods are provided with concave grooves for arranging a wire.

In the pressure-preserving conventional triaxial compression loading apparatus of the present invention, an upper limit assembly of the upper piston rod is disposed on an upper end surface of the upper cylinder cover, and a lower limit assembly of the lower piston rod is disposed on a lower end surface of the lower cylinder cover.

In the pressure-preserving conventional triaxial compression loading apparatus of the present invention, an upper load sensor and an upper displacement meter for measuring the upper piston rod are further disposed on the upper end surface of the upper cylinder cover, and a lower load sensor and a lower displacement meter for measuring the lower piston rod are disposed on the lower end surface of the lower cylinder cover.

In the pressure-preserving conventional triaxial compression loading apparatus of the present invention, the measuring sensors include a radial displacement sensor, an acoustic emission detector, and a thermometer, and a heating rod or a cooling rod is further disposed in the oil bag support.

In the pressure-preserving conventional triaxial compression loading apparatus of the present invention, an upper platen assembly is disposed on the lower end surface of the upper piston rod, a lower platen assembly is disposed on the upper end surface of the lower piston rod, the upper platen assembly and the lower platen assembly have the same structure, each of the upper platen assembly and the lower platen assembly includes a platen fixed on an end surface of a piston rod and a transverse wave velocity probe, a longitudinal wave velocity probe, and an acoustic emission probe that are mounted on the platen and are in contact with the fidelity specimen, through holes in communication with the platens of the upper and lower platen assemblies are respectively provided at axes of the upper and lower piston rods, a measurement apparatus measuring an axial displacement is capable of being placed in each through hole, and the platens of the upper and lower platen assemblies respectively fit the through holes at the axes of the upper and lower piston rods in a sealed manner.

In the pressure-preserving conventional triaxial compression loading apparatus of the present invention, a thermal insulation lining is disposed on the outer wall of the annular oil bag, and is used for attenuating heat transfer between the annular inner chamber of the annular oil bag and the oil bag support and the inner wall of the confining pressure chamber.

In the pressure-preserving conventional triaxial compression loading apparatus of the present invention, the lower sealing assembly includes a rotary seal ring and a positioning clamping ring, several limiting blocks protruding inward are arranged at intervals in a circumferential direction on an inner side surface of a lower port of the lower cylinder block, clamping blocks corresponding to the limiting blocks are disposed in a circumferential direction on an outer side surface of a lower end of the rotary seal ring, the clamping blocks of the rotary seal ring are separately inserted into clamping grooves between the limiting blocks of the lower cylinder block from the lower end, then continue to move upward to be above the limiting blocks, and rotate to clamp the clamping blocks between upper end surfaces of the limiting blocks and a hole shoulder in the lower chamber, an inner side surface of the rotary seal ring fits the lower piston rod in a sealed manner, an outer side surface of an upper end of the rotary seal ring fits an inner wall of the lower chamber in a sealed manner, positioning blocks that protrude outward and correspond to the clamping grooves between the limiting blocks are disposed in a circumferential direction on an outer side surface of the positioning clamping ring, upper end surfaces of the positioning blocks are higher than an upper end surface of the positioning clamping ring, and after the positioning blocks are inserted in the clamping grooves between the limiting blocks and clamping grooves between the clamping blocks, the upper end surface of the positioning clamping ring fits a lower end surface of the rotary seal ring, and a lower end surface of the positioning clamping ring is flush with a lower end surface of the lower cylinder block.

A method for performing a pressure-preserving conventional triaxial loading test on a fidelity specimen using the pressure-preserving conventional triaxial compression loading apparatus is proposed in the present invention. The pressure-preserving conventional triaxial compression loading apparatus containing the fidelity specimen is first placed upright on a uniaxial tester, then a hydrostatic pressure test, a deviatoric stress compression test, a free-end extrusion test, or a fixed-end extrusion test is separately performed on the fidelity specimen, the four kinds of tests are performed according to the need without sequence requirements, and specific methods of every test are separately as follows:

a. in the hydrostatic pressure test, the annular inner chamber of the annular oil bag is in communication with hydraulic pipes of the upper balance chamber and the lower balance chamber, and a hydrostatic pressure is synchronously applied to the fidelity specimen; in this case, no external load is applied to the upper and lower piston rods, the air pressure in the upper compensation chamber is increased to compensate for impact of the gravity of an upper piston, and the air pressure in the lower compensation chamber is decreased to compensate for impact of the gravity of a lower piston; axial and radial deformations of the fidelity specimen, an acoustic velocity change, and an acoustic emission event are measured in the test when the hydrostatic pressure changes; and during the test, a pore pressure is capable of being servo controlled to remain unchanged, and a volume of a pore fluid flowing into or flowing out of the specimen chamber is measured, or an inlet or outlet of the specimen chamber is capable of being closed to measure a change in the pore pressure;

b. in the deviatoric stress compression test, the annular inner chamber of the annular oil bag is in communication with hydraulic pipes of the upper balance chamber and the lower balance chamber, a hydrostatic pressure is synchronously applied to the fidelity specimen, and external load is applied to ends of the upper and lower piston rods to cause the upper and lower piston rods to actively move; axial and radial deformations of the fidelity specimen, an acoustic velocity change, and an acoustic emission event are measured in different combinations of a hydrostatic pressure and a deviatoric stress; and during the test, a pore pressure is capable of being servo controlled to remain unchanged, and a volume of a pore fluid flowing into or flowing out of the specimen chamber is measured, or an inlet or outlet of the specimen chamber is capable of being closed to measure a change in the pore pressure;

c. in the free-end extrusion test, hydraulic pipes of the upper balance chamber, the lower balance chamber, and the annular inner chamber of the annular oil bag are independent of each other and are not in communication, hydraulic pressures in the upper balance chamber and the lower balance chamber are servo controlled to be equal to a pore pressure of the specimen in the specimen chamber, axial movements of the piston rods are not limited, a hydraulic pressure in the annular inner chamber of the annular oil bag is increased, and an annular extrusion force is applied to the fidelity specimen; axial and radial deformations of the fidelity specimen, an acoustic velocity change, and an acoustic emission event during extension are measured under different extrusion forces; and during the test, the pore pressure is capable of being servo controlled to remain unchanged, and a volume of a pore fluid flowing into or flowing out of the specimen chamber is measured, or an inlet or outlet of the specimen chamber is capable of being closed to measure a change in the pore pressure;

d. in the fixed-end extrusion test, hydraulic pipes of the upper balance chamber, the lower balance chamber, and the annular inner chamber of the annular oil bag are independent of each other and are not in communication, hydraulic pressures in the upper balance chamber and the lower balance chamber are servo controlled to be equal to a pore pressure of the specimen in the specimen chamber, the piston rods are fixed, a hydraulic pressure in the annular inner chamber of the annular oil bag is increased, and an annular extrusion force is applied to the fidelity specimen; axial and radial deformations of the fidelity specimen, an acoustic velocity change, and an acoustic emission event are measured under different extrusion forces when extension of the specimen is restricted; and during the test, the pore pressure is capable of being servo controlled to remain unchanged, and a volume of a pore fluid flowing into or flowing out of the specimen chamber is measured, or an inlet or outlet of the specimen chamber is capable of being closed to measure a change in the pore pressure.

Compared with the prior art, the pressure-preserving conventional triaxial compression loading apparatus in the present invention has the following beneficial effects: The specimen chamber defined by the upper piston rod, the lower piston rod, and the inner wall of the annular oil bag accommodates a fidelity specimen. The pressure in the upper and lower balance chambers, the annular inner chamber of the annular oil bag, and the specimen chamber are set respectively to preserve pore pressure of the fidelity specimen, to ensure a pressure-preserving state of the fidelity specimen. The annular oil bag and the upper and lower piston rods are used to apply additional loading, to implement a pressure-preserving conventional triaxial loading test on the fidelity specimen. A variety of measuring sensors disposed in the annular inner chamber of the annular oil bag are used to obtain the test data when performing the pressure-preserving conventional triaxial loading test on the fidelity specimen. Therefore, it resolve the problem that a triaxial tester in the prior art cannot perform pressure-preserving loading and testing on a fidelity specimen, so that the test data is more accurate and reliable, to help to study the mechanical behavior of in-situ rock and measure their mechanical properties more faithfully.

Embodiments of the pressure-preserving conventional triaxial compression loading apparatus of the present invention are further described below with reference to the accompanying drawings.

DETAILED DESCRIPTION

Figure 1:
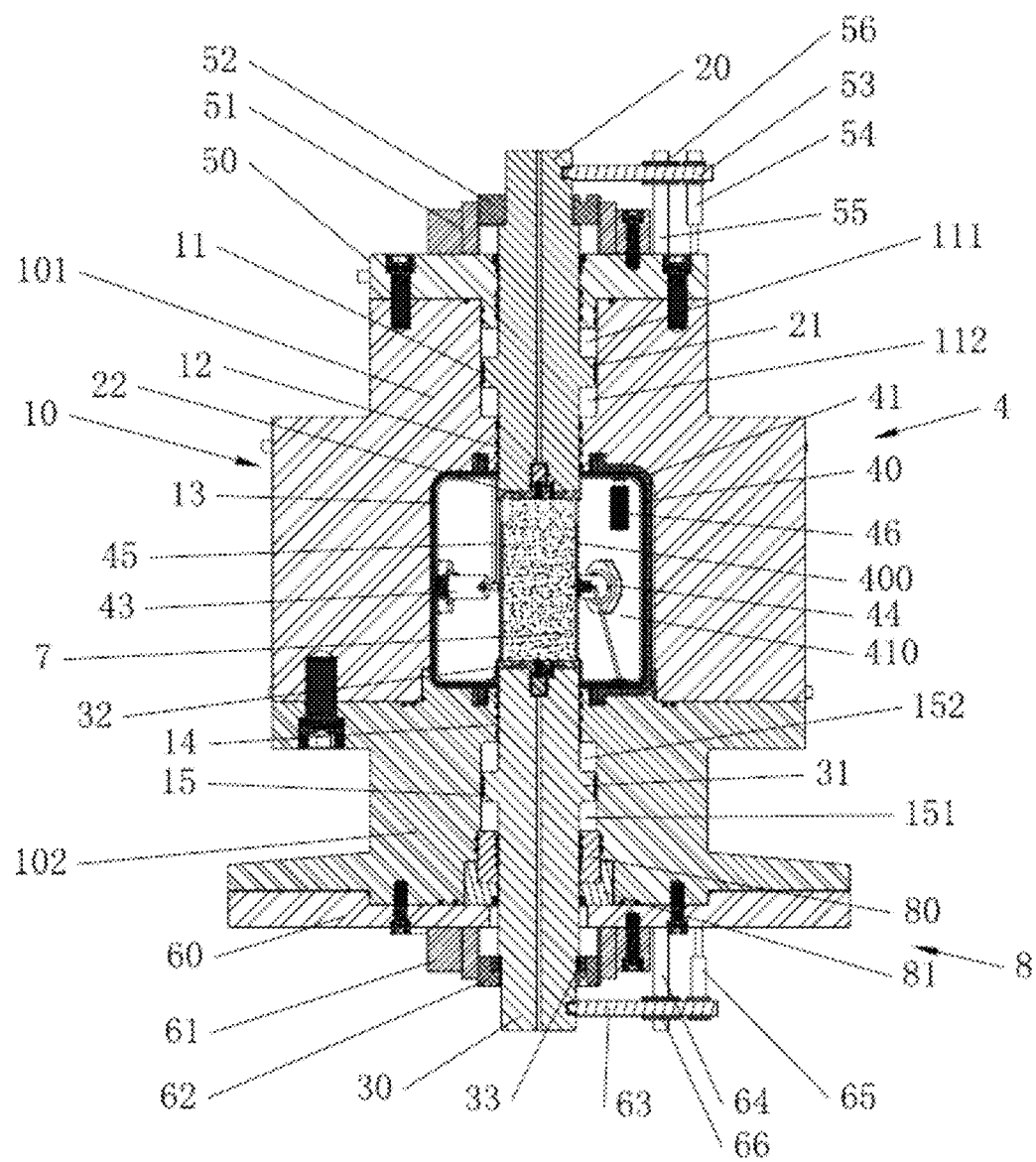
FIG. 1 is a front sectional view of a pressure-preserving conventional triaxial compression loading apparatus according to the present invention.
Figure 2:
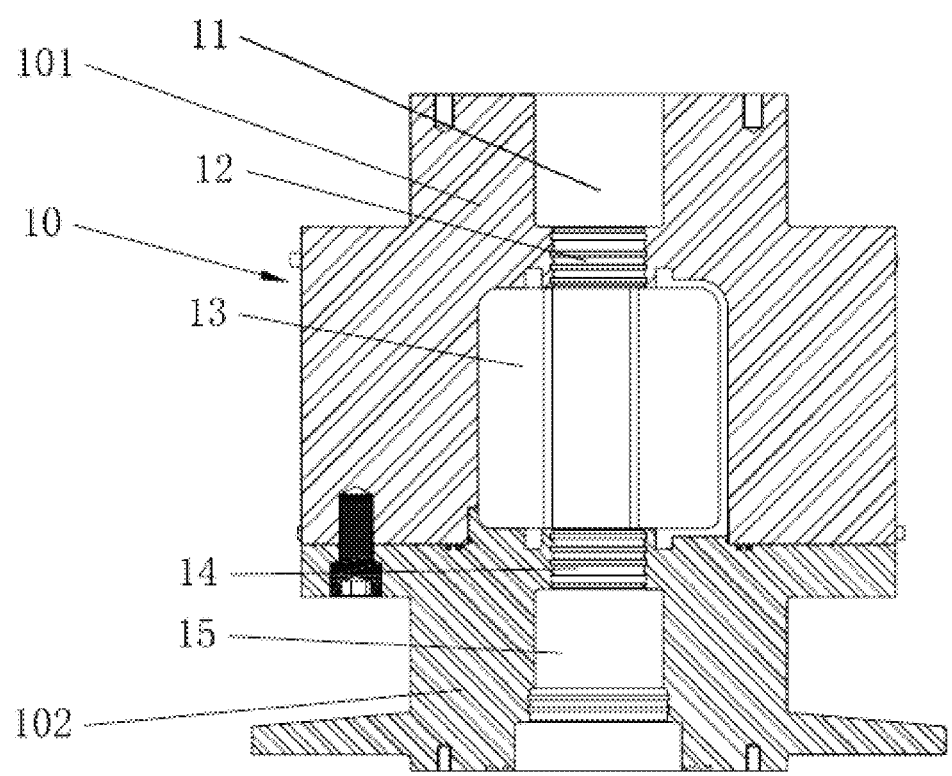
FIG. 2 is a sectional view of a pressure vessel of a pressure-preserving conventional triaxial compression loading apparatus according to the present invention.

As shown in FIG. 1, a pressure-preserving conventional triaxial compression loading apparatus of the present invention includes a pressure vessel 10, an upper piston rod 20, a lower piston rod 30, and an annular oil bag assembly 4. The pressure vessel 10 is formed by connecting an upper cylinder block 101 and a lower cylinder block 102 using bolts in a sealed manner. An upper annular boss 21 is disposed in the middle of the upper piston rod 20. An annular area of the upper annular boss 21 is equal to a cross-sectional area of the upper piston rod 20. A lower annular boss 31 is disposed in the middle of the lower piston rod 30. An annular area of the lower annular boss 31 is equal to a cross-sectional area of the lower piston rod 30. As shown in FIG. 2, hollow chambers of the pressure vessel 10 in vertical communication sequentially include an upper chamber 11, an upper sealed chamber 12, a confining pressure chamber 13, a lower sealed chamber 14, and a lower chamber 15 from top to bottom. The upper chamber 11 and the upper sealed chamber 12 are located in the upper cylinder block 101. The lower sealed chamber 14 and the lower chamber 15 are located in the lower cylinder block 102. The confining pressure chamber 13 is formed by connecting the upper cylinder block 101 and the lower cylinder block 102 in a sealed manner. As shown in FIG. 1, an upper cylinder cover 50 is fixed on an upper end surface of the upper cylinder block 101 by a bolt and fits an upper port of the upper chamber 11 in a sealed manner. The upper piston rod 20 located below the upper annular boss 21 fits the upper sealed chamber 12 in a sealed manner. The upper annular boss 21 fits the upper chamber 11 in a sealed manner. The upper piston rod 20 located above the upper annular boss 21 passes upward through the upper cylinder cover 50 to fit the upper cylinder cover 50 in a sealed manner. The upper annular boss 21 of the upper piston rod 20 divides the upper chamber 11 into two chambers independent of each other. The two chambers are an upper balance chamber 111 located above the upper annular boss and an upper compensation chamber 112 located below the upper annular boss. An upper limit assembly of the upper piston rod 20, an upper load sensor 51, and an upper displacement meter 54 are disposed on an upper end surface of the upper cylinder cover 50. The upper load sensor 51 is fixed on the upper end surface of the upper cylinder cover 50 by bolts. The upper limit assembly includes an upper limit ring 52 and an upper limit rod 53. The upper limit ring 52 is used for limiting an upward movement limit position of the upper piston rod 20. The upper limit rod 53 is used for preventing the upper piston rod 20 from rotating. The upper limit ring 52 is threadedly connected to an inner threaded hole of the upper load sensor 51. An inner hole of the upper limit ring 52 forms a clearance fit with the upper piston rod 20. A lower end surface of the upper limit ring 52 is capable of fitting a shaft shoulder at an upper end of the upper piston rod 20, and is used for limiting the upper piston rod 20 from continuing to move upward. A vertical height of the upper limit ring 52 is capable of being adjusted by rotating the upper limit ring 52, thereby adjusting an upper limit position of the upper piston rod. When the upper piston rod 20 moves upward to a limit position of the upper piston rod, the upper load sensor 51 is used for measuring load that the upper load sensor bears. The upper limit rod 53 is placed horizontally. One end of the upper limit rod is fixedly connected to the upper piston rod 20 located above the upper limit ring 52, and the other end of the upper limit rod is fixedly connected to an upper slider 56. The upper slider 56 is mounted on an upper slide support 55 in a vertically slidable manner. The upper slide support 55 is fixed on the upper cylinder cover 50. A housing at an upper end of the upper displacement meter 54 is fixedly connected to the upper limit rod 53. A probe rod at a lower end of the upper displacement meter abuts against the upper end surface of the upper cylinder cover 50 and is used for measuring a displacement of the upper piston rod 20.

As shown in FIG. 1, a lower port of the lower chamber 15 of the lower cylinder block 102 is provided with a lower sealing assembly 8 fitting the lower port in a sealed manner. A lower end surface of the lower sealing assembly 8 is flush with a lower end surface of the lower cylinder block 102. A lower cylinder cover 60 covers the lower end surfaces of the lower cylinder block 102 and the lower sealing assembly 8, and is fixedly connected to the lower cylinder block 102 using bolts. The lower piston rod 30 located above the lower annular boss 31 fits the lower sealed chamber 14 in a sealed manner. The lower annular boss 31 fits the lower chamber 15 in a sealed manner. The lower piston rod 30 located below the lower annular boss 31 sequentially passes downward through an inner hole of the lower sealing assembly 8 and the lower cylinder cover 60. The lower piston rod 30 fits the inner hole of the lower sealing assembly 8 in a sealed manner. The lower annular boss 31 of the lower piston rod 30 divides the lower chamber 15 into two chambers independent of each other. The two chambers are a lower balance chamber 151 located below the lower annular boss and a lower compensation chamber 152 located above the lower annular boss. A lower limit assembly of the lower piston rod 30, a lower displacement meter 65, and a lower load sensor 61 for measuring a load that the lower piston rod 30 bears are disposed on a lower end surface of the lower cylinder cover 60. The lower load sensor 61 is fixed on the lower end surface of the lower cylinder cover 60 by bolts. The lower limit assembly includes a lower limit ring 62 and a lower limit rod 63. The lower limit ring 62 is used for limiting a downward movement limit position of the lower piston rod 30. The lower limit rod 63 is used for preventing the lower piston rod 30 from rotating. The lower limit ring 62 is threadedly connected to a threaded hole of the lower load sensor 61. An upper end of the lower limit ring 62 can fit a blocking ring 33 at a lower portion of the lower piston rod 30, and is used for limiting the lower piston rod 30 from continuing to move downward. A vertical height of the lower limit ring 62 is capable of being adjusted by rotating the lower limit ring, thereby adjusting a lower limit position of the lower piston rod 30. Before the lower piston rod 30 is pushed into the pressure vessel, the lower sealing assembly 8 is first sleeved over the lower piston rod 30, and then the blocking ring 33 is threadedly connected to the lower piston rod 30. The blocking ring 33 can further prevent the lower sealing assembly 8 from sliding out from the lower piston rod 30. The lower limit rod 63 is placed horizontally. One end of the lower limit rod is fixedly connected to the lower piston rod 30 located below the lower limit ring 62, and the other end of the lower limit rod is fixedly connected to a lower slider 66. The lower slider 66 is mounted on a lower slide support 64 in a vertically slidable manner. The lower slide support 64 is fixed on the lower cylinder cover 60. A housing at a lower end of the lower displacement meter 65 is connected to the lower limit rod 63. A probe rod at an upper end of the lower displacement meter abuts against the lower end surface of the lower cylinder cover 60 and is used for measuring a displacement of the lower piston rod 30.

Figure 3:
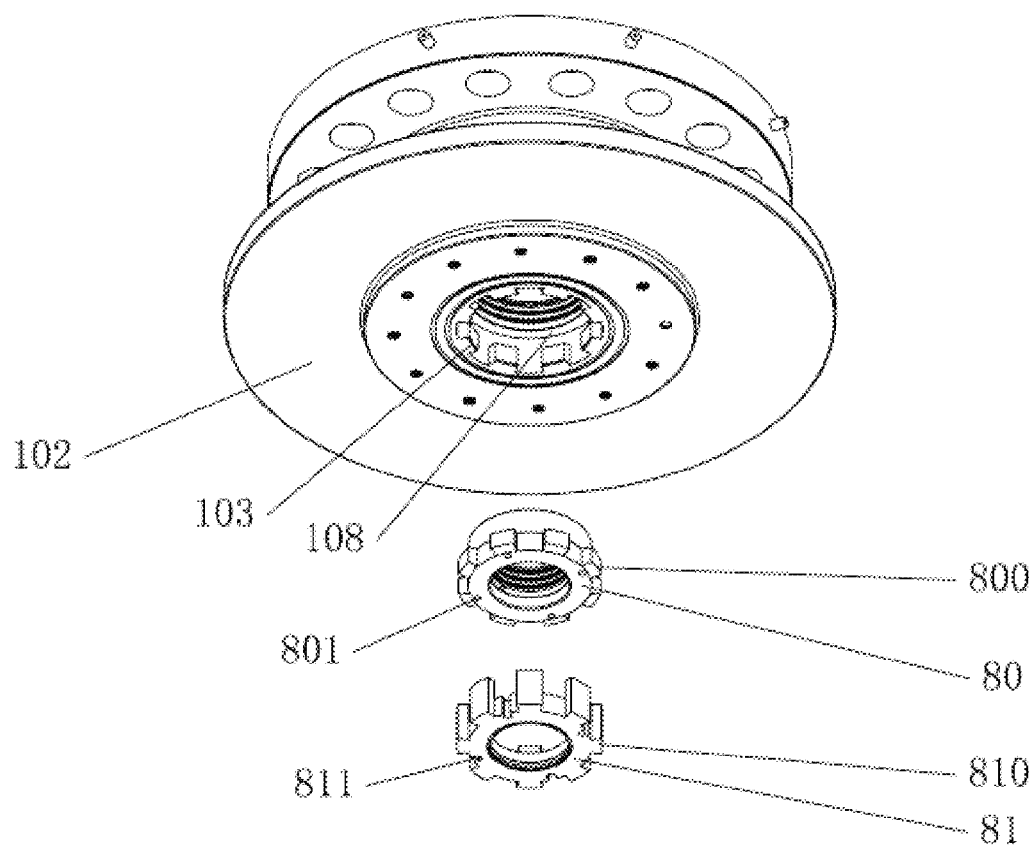
FIG. 3 is a schematic exploded view of a lower cylinder block, a rotary seal ring, and a positioning clamping ring of a pressure-preserving conventional triaxial compression loading apparatus according to the present invention.
Figure 6:
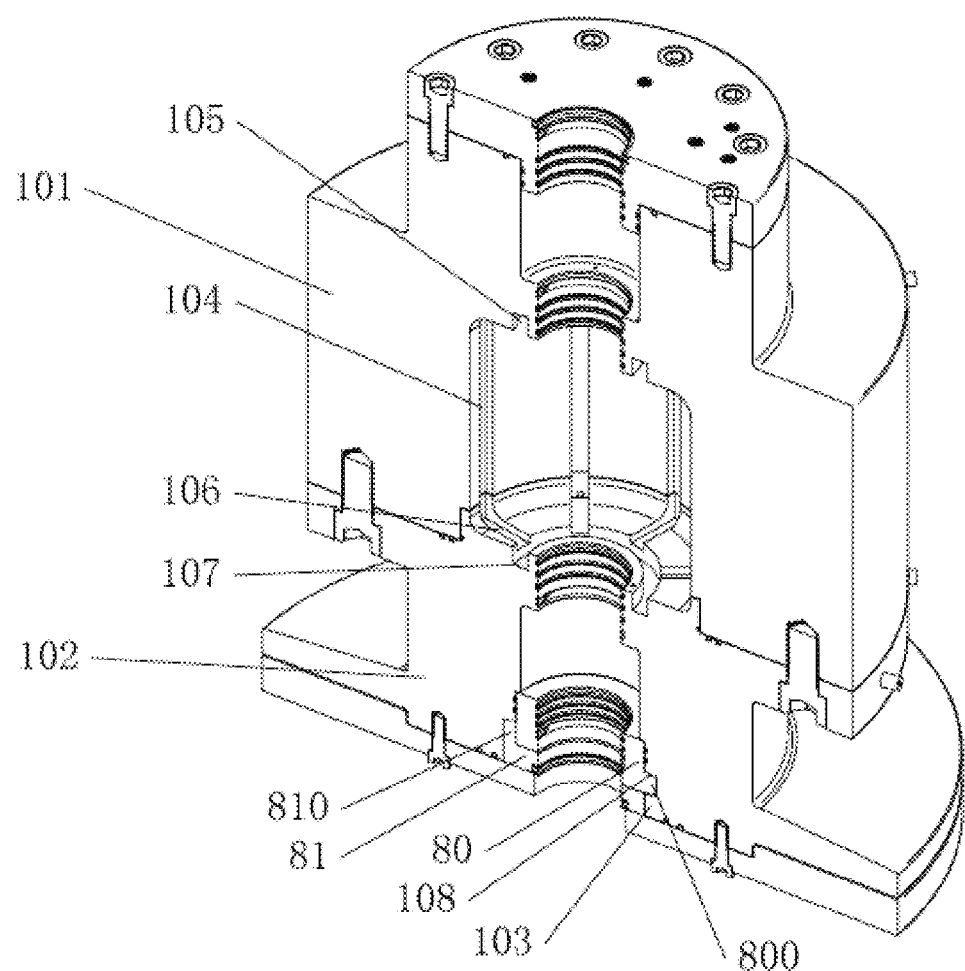
FIG. 6 is a three-dimensional schematic diagram of a pressure vessel fitting a lower sealing assembly of a pressure-preserving conventional triaxial compression loading apparatus according to the present invention.

As shown in FIG. 3 and FIG. 6, the lower sealing assembly 8 includes a rotary seal ring 80 and a positioning clamping ring 81. Eight limiting blocks 103 that protrude inward and are arranged at equal distances are disposed in a circumferential direction on an inner side surface of the lower port of the lower chamber 15 of the lower cylinder block 102. (A quantity of the limiting blocks 103 may be designed according to an actual requirement). Eight clamping blocks 800 that protrude outward and correspond to the limiting blocks 103 are disposed on an outer side surface of a lower end of the rotary seal ring 80. The clamping blocks 800 may pass through clamping grooves between the limiting blocks 103. The clamping blocks 800 of the rotary seal ring 80 are separately inserted into the clamping grooves between the limiting blocks 103 from the lower end, then continue to move upward to be above the limiting blocks 103, and rotate to clamp the clamping blocks 800 between upper end surfaces of the limiting blocks 103 and a hole shoulder 108 in the lower cylinder block 102. An inner side surface of the rotary seal ring 80 fits the lower piston rod 30 in a sealed manner. An outer side surface of an upper end of the rotary seal ring 80 fits the lower chamber 15 in a sealed manner (referring to FIG. 1). Several rotation positioning holes 801 are provided in a lower end surface of the rotary seal ring 80, and are used for implementing rotation driving of the lower sealing assembly. Four rotation positioning holes 801 are provided in this embodiment, and are all distributed at equal intervals in a circumferential direction. Positioning blocks 810 that correspond to the clamping grooves between the limiting blocks 103 and protrude outward are disposed in a circumferential direction on an outer side surface of the positioning clamping ring 81. Upper end surfaces of the positioning blocks 810 are higher than an upper end surface of the positioning clamping ring 81. After the positioning blocks 810 are inserted in the clamping grooves between the limiting blocks 103 and clamping grooves between the clamping blocks 800, the upper end surface of the positioning clamping ring 81 fits the lower end surface of the rotary seal ring 80, and a lower end surface of the positioning clamping ring 81 is flush with the lower end surface of the lower cylinder block 102. The lower cylinder cover 60 covers the lower end surfaces of the lower cylinder block 102 and the positioning clamping ring 81, and is fixed on the lower cylinder block 102 by bolts. The positioning clamping ring 81 can effectively prevent the rotary seal ring 80 from falling downward due to rotation. Rotation concave grooves 811 corresponding to the rotation positioning holes 801 in the rotary seal ring 80 are provided in the outer side surface of the positioning clamping ring 81. When the positioning blocks 810 of the positioning clamping ring 81 are inserted in the clamping grooves of the rotary seal ring 80, the rotation positioning holes 801 can correspond to the rotation concave grooves 811.

As shown in FIG. 1, an upper platen assembly 22 is mounted on a lower end surface of the upper piston rod 20. A lower platen assembly 32 is mounted on an upper end surface of the lower piston rod 30. The upper platen assembly 22 and the lower platen assembly 32 have the same structure. Each of the upper platen assembly and the lower platen assembly includes a platen with a T-shaped central cross section and a transverse wave velocity probe, a longitudinal wave velocity probe, and an acoustic emission probe that are mounted on the platen and are in contact with a fidelity specimen 7. Through holes in communication with upper ends of the upper and lower platens are respectively provided at axes of the upper and lower piston rods 20, 30. A measurement apparatus measuring an axial displacement is capable of being placed in each through hole. The platens of the upper and lower platen assemblies respectively fit the through holes at the axes of the upper and lower piston rods in a sealed manner. One end of the platen is pressed on an end surface of the upper piston rod 20 or the lower piston rod 30 and is fixed with a piston rod by bolts, and the other end is used for being pressed on an upper end surface or a lower end surface of the fidelity specimen 7.

Figure 4:
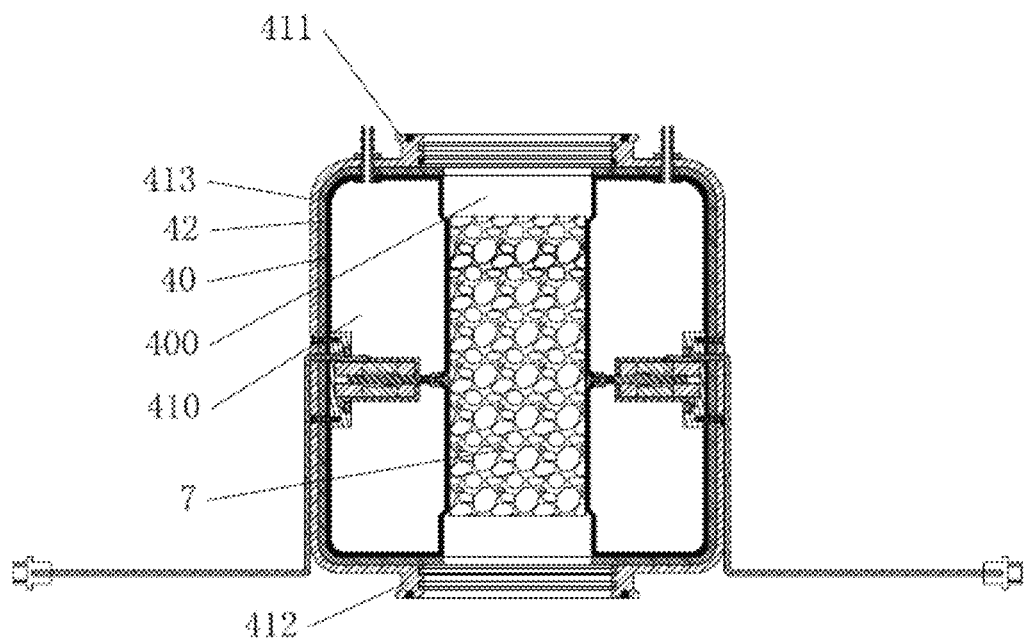
FIG. 4 is a schematic diagram of an oil bag assembly of a pressure-preserving conventional triaxial compression loading apparatus according to the present invention.
Figure 5:
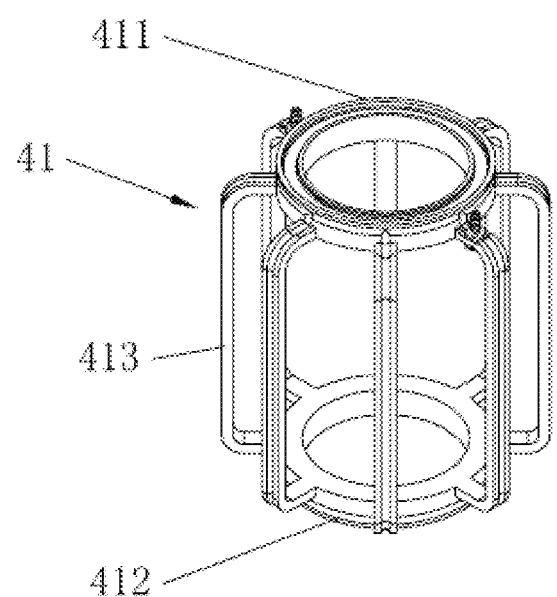
FIG. 5 is a three-dimensional schematic diagram of an oil bag support of a pressure-preserving conventional triaxial compression loading apparatus according to the present invention.

As shown in FIG. 4 and FIG. 5, the annular oil bag assembly 4 includes an oil bag support 41 and an annular oil bag 40 fixed in the oil bag support 41. The annular oil bag assembly 4 is placed in the confining pressure chamber 13. To perform high and low temperature tests, in this embodiment, a thermal insulation lining 42 is stuck on an outer wall of the annular oil bag 40, so that heat transfer between hydraulic oil in an annular inner chamber 410 of the annular oil bag 40 and the oil bag support 41 and an inner wall of the confining pressure chamber 13 can be effectively attenuated, to help to control of the temperature of the hydraulic oil in the annular inner chamber 410. In addition, a heating rod 46 and a thermometer 45 are disposed in the annular inner chamber 410 for heating and temperature measurement of the hydraulic oil. According to a design requirement, if necessary, it may be further considered to arrange a cooling rod in the annular inner chamber 410 to reduce the temperature of the hydraulic oil. During actual application, it may be selected according to an actual test requirement whether to add the thermal insulation lining 42. The oil bag support 41 includes an upper annular body 411, a lower annular body 412, and eight connecting rods 413. Each connecting rod 413 is a C-shaped body protruding outward. An upper end of the connecting rod 413 is fixed on an outer side surface of the upper annular body 411. A lower end of the connecting rod 413 is fixed on an outer side surface of the lower annular body 412. The upper annular body 411, the lower annular body 412, and the connecting rods 413 of the oil bag support may be integrally formed or separately processed and then fixedly connected. The integral formation is used in this embodiment, and the integral formation can ensure the stiffness and accuracy of the oil bag support. An upper end and a lower end of the annular oil bag 40 are respectively pasted to a lower end surface of the upper annular body 411 and an upper end surface of the lower annular body 412. The oil bag support 41 is inserted in a concave groove that is in the inner wall of the confining pressure chamber 13 and fits the oil bag support. End surfaces and inner side surfaces of the upper annular body 411 and the lower annular body 412 fit the concave groove in the inner wall of the confining pressure chamber 13 in a sealed manner. The outer side surfaces of the upper annular body 411 and the lower annular body 412 and outer side surfaces of the connecting rods 413 are provided with concave grooves for arranging a wire. When the annular inner chamber 410 of the annular oil bag 40 is filled with the hydraulic oil, the outer side wall of the annular oil bag 40 and an inner wall of the oil bag support 41 are attached together, and the outer wall of the annular oil bag 40 between the connecting rods 413 and the inner wall of the confining pressure chamber 13 are attached together. The fidelity specimen 7 is placed in a specimen chamber 400 defined by the lower end surface of the upper piston rod 20, the upper end surface of the lower piston rod 30, and an inner wall of the annular oil bag 40. As shown in FIG. 1, a variety of measuring sensors are disposed in the annular inner chamber 410 of the annular oil bag 40. The measuring sensors include a radial displacement sensor 43, an acoustic emission detector 44, and the thermometer 45. After wires of the measuring sensors installed in the annular inner chamber 410 pass through an oil bag wall of the annular oil bag 40 and the connecting rods 413 of the oil bag support 41 in a sealed manner, the wires are arranged along the concave grooves located on an outer side of the oil bag support 41, and are finally led out from a wire hole in a sidewall of a lower portion of the upper cylinder block 101. A temperature and pressure resistant sealed wiring terminal is mounted at an end portion of the wire hole.

The annular inner chamber 410, the specimen chamber 400, the upper balance chamber 111, the upper compensation chamber 112, the lower balance chamber 151, and the lower compensation chamber 152 are chambers independent of each other and are separately provided with corresponding fluid inlet and outlet pipes. In this embodiment, each of the upper compensation chamber 112 and the lower compensation chamber 152 is provided with one air inlet and one air outlet, and connected pipes are pneumatic piping. Each of the annular inner chamber 410, the upper balance chamber 111, and the lower balance chamber 151 is provided with one oil inlet and one oil outlet, and connected pipes are hydraulic piping. One liquid inlet and one liquid outlet are provided at an upper end of the specimen chamber 400, one liquid inlet and one liquid outlet are also provided at a lower end of the specimen chamber, and connected pipes are hydraulic piping.

A method for assembling the pressure-preserving conventional triaxial compression loading apparatus in the present invention is as follows: First, as shown in FIG. 1, the assembled annular oil bag assembly 4 is placed in from a lower port of the upper cylinder block 101. As shown in FIG. 6, the connecting rods 413 of the oil bag support 41 are inserted along upper connecting rod grooves 104 that correspond to the connecting rods and are in an inner wall of the upper cylinder block 101, it is ensured that the upper annular body 411 of the oil bag support 41 is inserted in an upper concave groove 105 in the upper cylinder block 101 corresponding to the upper annular body, and the wires of the measuring sensors in the annular oil bag 40 are connected. Next, the lower cylinder block 102 is connected to the upper cylinder block 101 in a sealed manner, so that lower connecting rod grooves 106 in the lower cylinder block 102 fit the connecting rods 413 on the oil bag support 41, a lower concave groove 107 in the lower cylinder block 102 fit the lower annular body 412 of the oil bag support 41, and the oil bag support 41 is fixed in the confining pressure chamber 13 formed by the upper cylinder block 101 and the lower cylinder block 102. Next, the upper piston rod 20 assembled with the upper platen assembly is inserted in the upper chamber 11 and the upper sealed chamber 12 of the upper cylinder block 101, and then the upper cylinder cover 50 and the upper limit assembly and the upper load sensor 51 on the upper cylinder cover 50 are fixed. After the foregoing mounting is completed, no disassembly is required in any subsequent test, unless a seal ring, a sensor or another part needs to be replaced.

Figure 7:
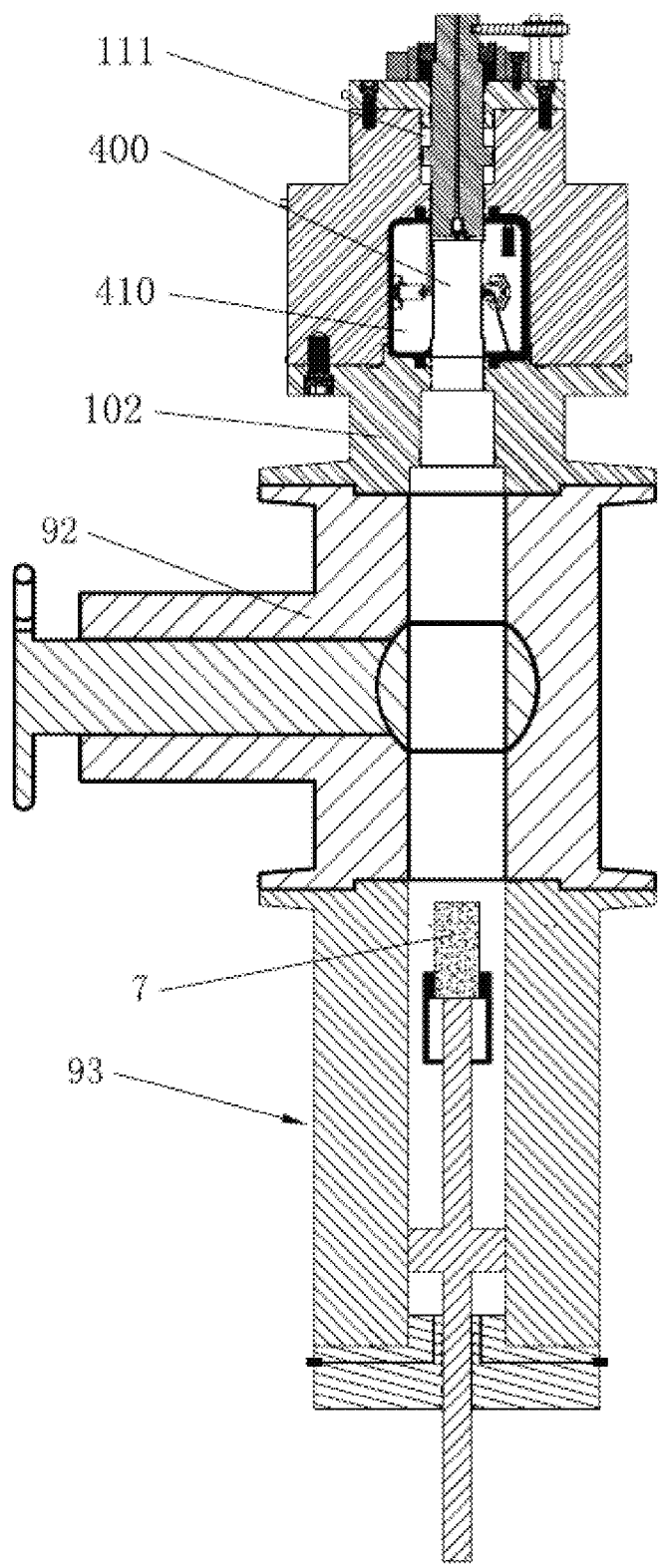
FIG. 7 is a schematic diagram of pressure-preserving pushing of a fidelity specimen from a specimen transport cabin to a pressure-preserving conventional triaxial compression loading apparatus according to the present invention.

Next, the fidelity specimen 7 is pushed into the specimen chamber 400 in a pressure-preserving state. As shown in FIG. 7, a valve cabin 92 connected to a specimen transport cabin 93 is mounted and fixed on a lower port of the lower cylinder block 102. The lower cylinder block 102 and the valve cabin 92 are fixed by bolts or fixed by a clamp. They are fixed by a clamp in this embodiment to facilitate disassembly. The valve cabin 92 is a pressure-resistant valve, and an appropriate valve type may be selected according to the pressure of pressure-preserving medium. Before the fidelity specimen 7 in the specimen transport cabin 93 is pushed, the upper limit ring 52 is rotated in advance to an appropriate position according to the height of the fidelity specimen 7, then hydraulic oil is injected into the annular inner chamber 410 and the upper balance chamber 111, and pressure-preserving medium same as that in the specimen transport cabin 93 is injected into the specimen chamber 400 and the lower chamber 15. The pressure of the oil in the specimen chamber 400 is adjusted to be equal to the pressure of the pressure-preserving medium containing the fidelity specimen 7, at the same time the pressure in the upper balance chamber 111 is adjusted to be equal to the pressure of the pressure-preserving medium, and the pressure of the oil in the annular inner chamber 410 of the annular oil bag 40 is adjusted to be slightly less than the pressure of the pressure-preserving medium in the specimen chamber 400 in the middle, to stretch the specimen chamber 400 so as to facilitate the entrance of the pushed fidelity specimen 7. The annular areas of the upper and lower annular bosses 21, 31 of the upper and lower piston rods 20, 30 are respectively equal to the cross-sectional areas of the upper and lower piston rods 20, 30. Therefore, pressures applied from the specimen chamber 400 to the upper and lower piston rods 20, 30 are respectively eliminated by pressures applied from the upper and lower balance chambers 111, 151 to the upper and lower piston rods 20, 30. The piston rods are in a force-balanced state and are not pushed outward by a high-pressure medium in the specimen chamber 400. After pressure values in the chambers are set, the valve cabin 92 is opened, and the fidelity specimen 7 is pushed in a pressure-preserving state from the specimen transport cabin 93 into the specimen chamber 400 in the middle of the annular oil bag 40. When the upper load sensor 51 displays that the upper piston rod 20 bears a pressure, it indicates that the fidelity specimen 7 has been mounted in position. Then the valve cabin 92 is closed, and the specimen transport cabin 93 is disassembled.

Figure 8:
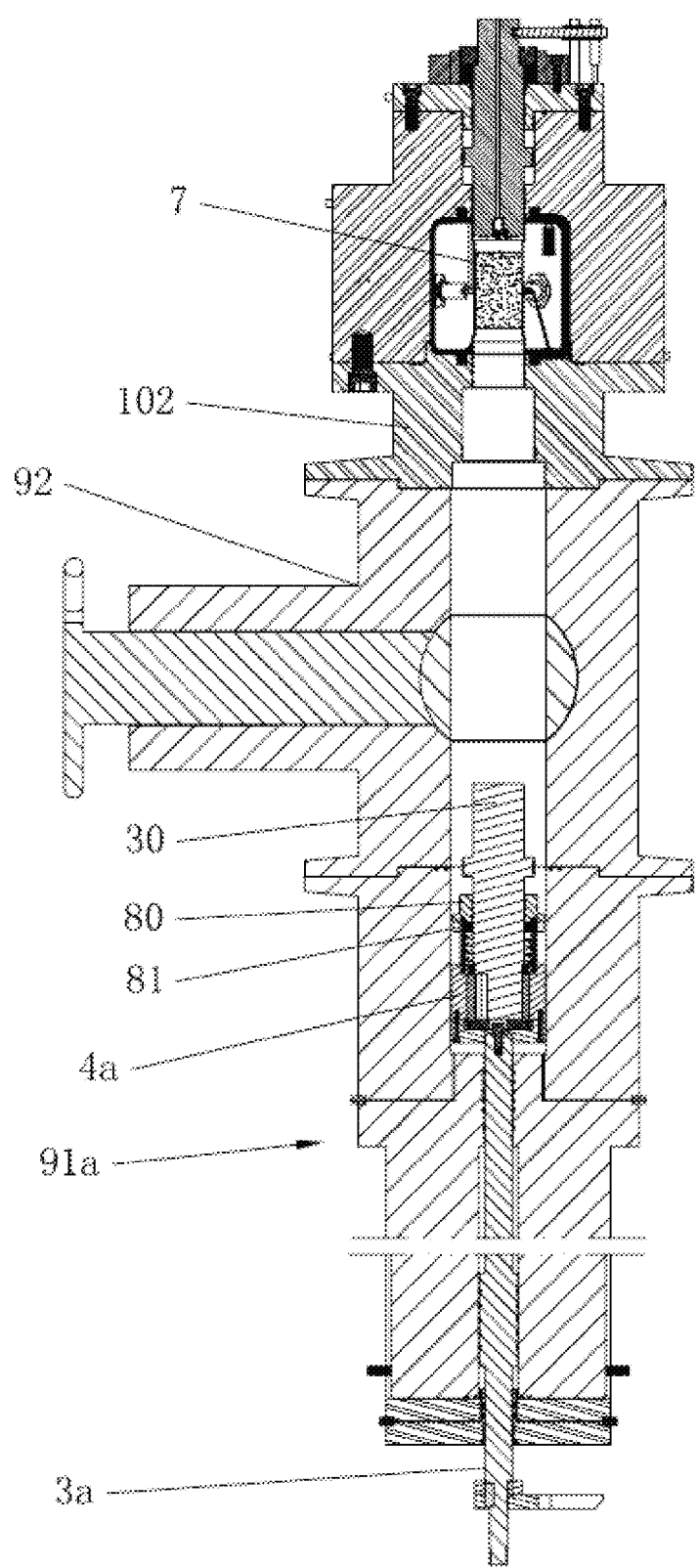
FIG. 8 is a schematic diagram of pressure-preserving pushing of a lower piston rod from a push rod cabin to a pressure-preserving conventional triaxial compression loading apparatus according to the present invention.
Figure 9:
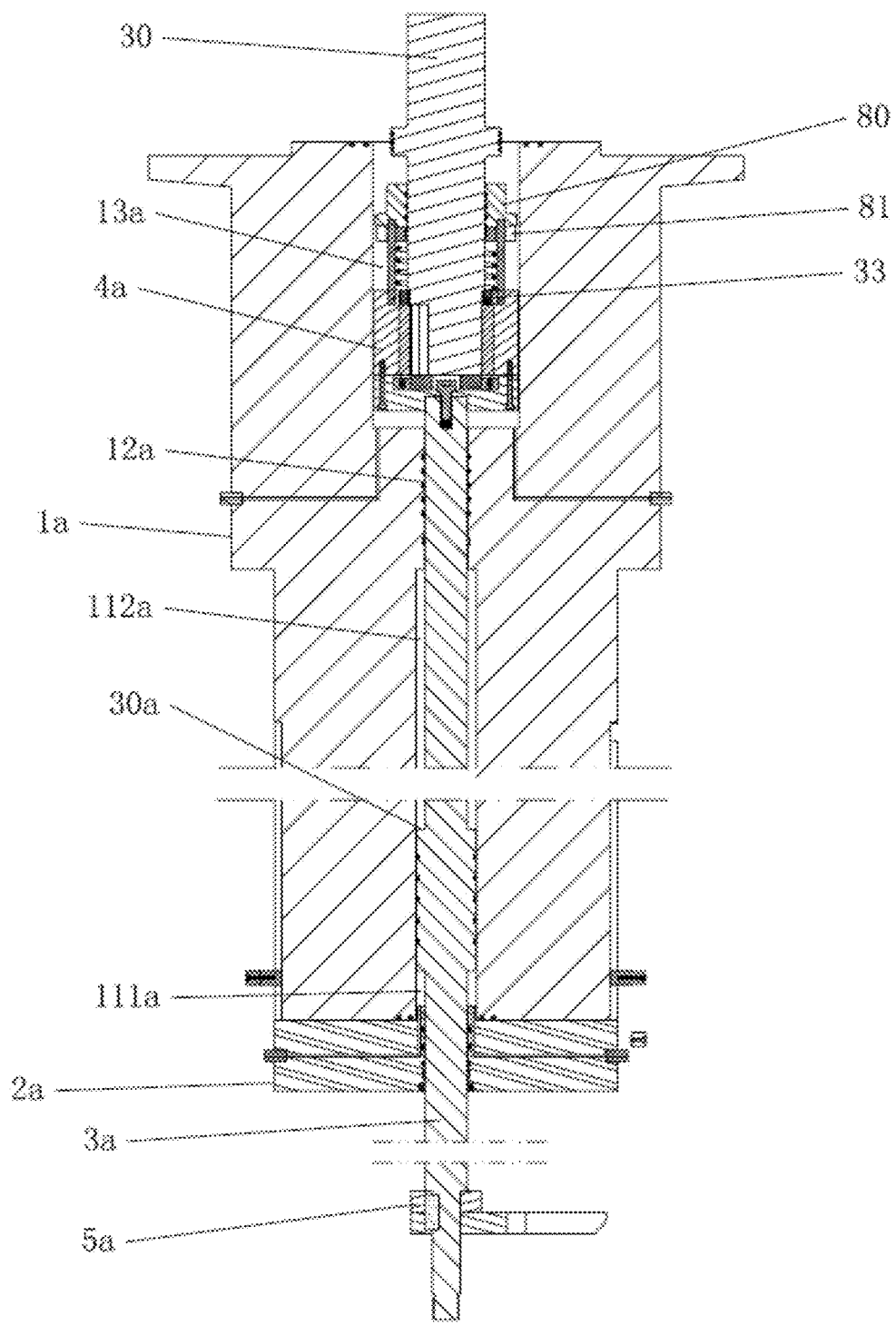
FIG. 9 is a schematic diagram after a lower piston rod and a lower sealing assembly of the present invention are mounted on a push rod.
Figure 10:
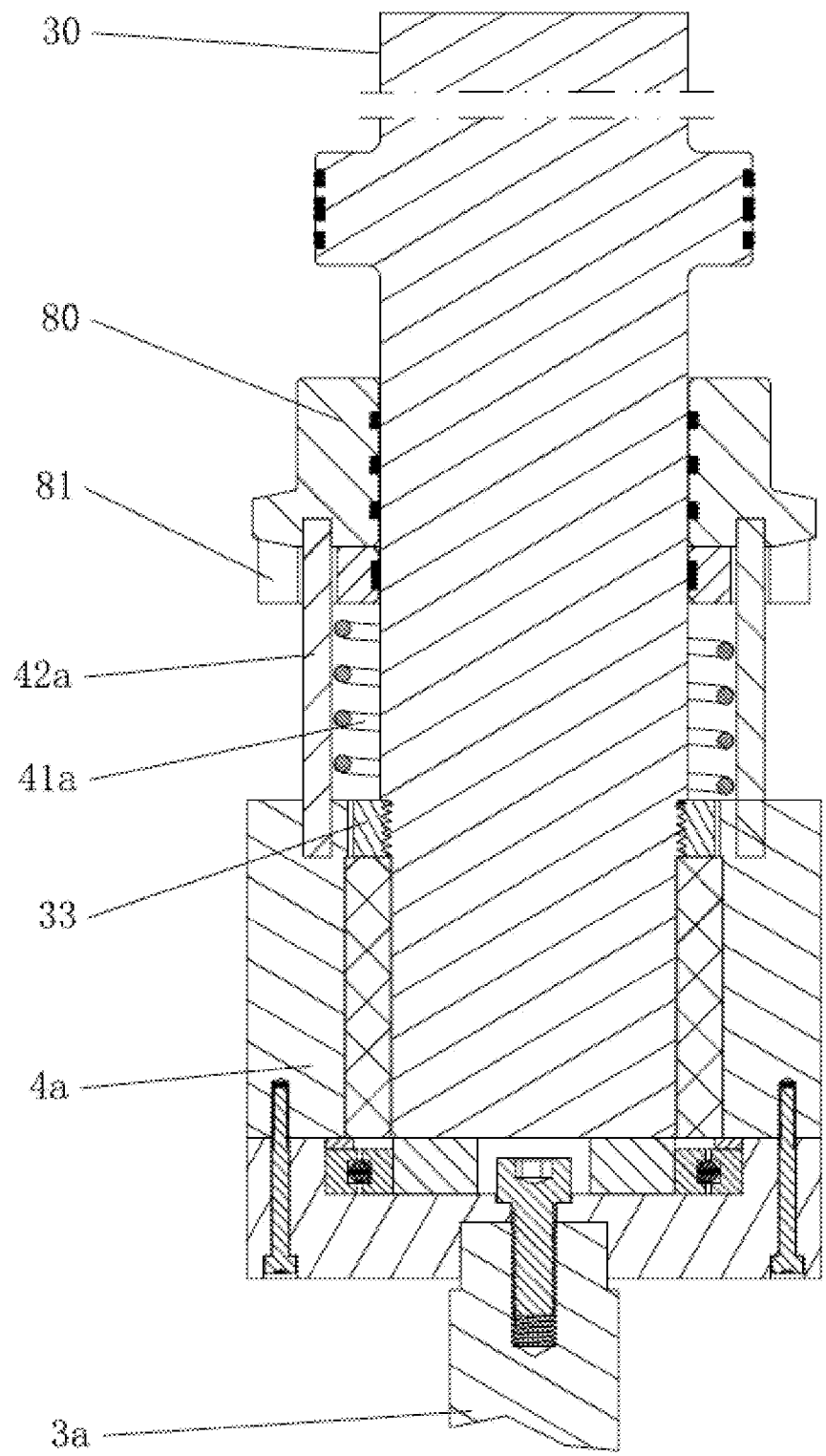
FIG. 10 is a schematic diagram after a push rod head is assembled together with a lower piston rod and a lower sealing assembly.

In the last step, a pressure-preserving push rod cabin 91a pushes the lower piston rod 30 and the lower sealing assembly 8 into the lower cylinder block 102 in a pressure-preserving state, and the lower sealing assembly 8 is used to implement pressure-preserving sealing. As shown in FIG. 9 and FIG. 10, the pressure-preserving push rod cabin 91a includes a cylinder block 1a, a cylinder cover 2a, and a push rod mechanism. Hollow chambers of the cylinder block 1a sequentially include a lower push rod chamber, a sealed chamber 12a, and an upper push rod chamber 13a from bottom to top. The cylinder cover 2a is fixed at a lower end of the cylinder block 1a in a sealed manner. The push rod mechanism includes a push rod driving apparatus 5a, a push rod 3a, and a push rod head assembly 4a fixedly connected to an upper end of the push rod 3a. Four rotating rods 42a capable of being respectively inserted in the rotation positioning holes 801 are disposed on an upper end surface of the push rod head assembly 4a. An annular boss 30a is disposed on the push rod 3a. An annular area of the annular boss 30a is equal to a cross-sectional area of the push rod 3a. The annular boss 30a is located in the lower push rod chamber and fits the lower push rod chamber in a sealed manner. The push rod 3a located on an upper side of the annular boss 30a fits the sealed chamber 12a in a sealed manner. The push rod 3a located on a lower side of the annular boss 30a passes through the cylinder cover 2a and fits the cylinder cover 2a in a sealed manner. The push rod 3a protruding from an outer side of the cylinder cover 2a is connected to the push rod driving apparatus 5a. The annular boss 30a divides the lower push rod chamber into two chambers. The two chambers are a first chamber 111a located on the lower side of the annular boss 30a and a second chamber 112a located on the upper side of the annular boss 30a. The push rod head assembly 4a is located in the upper push rod chamber 13a. Before the lower piston rod 30 is pushed, the lower sealing assembly 8 first needs to be sleeved over the lower piston rod 30, then a blocking ring 33 is threadedly connected to the lower piston rod 30, and then a spring 41a is sleeved over the lower piston rod 30. After the lower piston rod 30 and the lower sealing assembly 8 are assembled together, a lower end of the lower piston rod 30 is inserted in a central hole at an upper end of the push rod head assembly 4a, and it is ensured that after passing through the rotation concave grooves 811, the rotating rods 42a on the upper end surface of the push rod head assembly 4a are inserted in the rotation positioning holes 801 corresponding to the rotating rods. In this case, a lower end of the spring 41a abuts against the upper end surface of the push rod head assembly 4a, and an upper end of the spring 41a abuts against a lower end surface of the lower sealing assembly 8. After the lower piston rod 30 and the lower sealing assembly 8 are mounted in the pressure-preserving push rod cabin 91a, as shown in FIG. 8, an upper port of the pressure-preserving push rod cabin 91a is connected to a lower port of the valve cabin 92 in a sealed manner. Then pipes of the first chamber 111a and the upper push rod chamber 13a are put in communication and filled with pressure-preserving medium, and the pressure is adjusted to be equal to the pressure in the pressure-preserving conventional triaxial compression loading apparatus in the present invention. The valve cabin 92 is opened to implement communication of pressure-preserving medium between the pressure-preserving conventional triaxial compression loading apparatus in the present invention and the pressure-preserving push rod cabin 91a. The push rod 3a is manually or electrically pushed to travel upward to drive the lower piston rod 30 and the lower sealing assembly 8 in the upper push rod chamber 13a to move upward. When the limiting blocks 103 in the lower cylinder block 102 of the pressure-preserving conventional triaxial compression loading apparatus in the present invention are reached, the rotary seal ring 80 passes through the clamping grooves between the limiting blocks 103 under the action of a pushing force to abut against the hole shoulder 108 in the lower chamber 15, and the positioning clamping ring 81 is stopped on an outer side of the limiting blocks 103. In this case, the spring 41a is tightly pressed to enter a compressed state. Then the push rod 3a is used to rotate the clamping blocks 800 of the rotary seal ring 80 to fit the upper end surfaces of the limiting blocks 103, to make the clamping blocks 800 of the rotary seal ring 80 clamped between the limiting blocks 103 and the hole shoulder 108 of the lower cylinder block 102. The positioning blocks 810 of the positioning clamping ring 81 are rotated to the clamping grooves between the limiting blocks 103. Under the action of the pushing force of the compressed spring 41a, the positioning blocks 810 of the positioning clamping ring 81 sequentially enter the clamping grooves between the limiting blocks 103 and the clamping grooves between the clamping blocks 800. The upper end surface of the positioning clamping ring 81 and the lower end surface of the rotary seal ring 80 fit together again, so that the rotary seal ring 80 can be effectively prevented from sliding out from the clamping grooves between the limiting blocks 103 due to rotation misalignment. Next, the pressure of the oil in the annular inner chamber 410 of the annular oil bag 40 is adjusted to be slightly greater than the pressure in the specimen chamber 400 in the middle, to make an oil bag wrap an outer side of a specimen as much as possible. The valve cabin 92 is closed, to discharge the pressure-preserving medium in the lower compensation chamber 152 and the lower balance chamber 151. Hydraulic oil is injected into the lower balance chamber 151. The pressure of the hydraulic oil in the lower balance chamber 151 is increased to be equal to the pressure of the pressure-preserving medium in the specimen chamber 400, and the pressure of the pressure-preserving medium at a connecting portion between the valve cabin and a test cabin is reduced simultaneously, and then the pressure-preserving medium is drained. The annular area of the lower annular boss 31 of the lower piston rod 30 is equal to a cross-sectional area of the lower end of the lower piston rod 30. Therefore, a pressure applied from the specimen chamber 400 to the lower piston rod 30 is eliminated by a pressure applied from the lower balance chamber 151 to the lower piston rod 30. The piston rods are in a force-balanced state and are not pushed outward by the high-pressure medium in the specimen chamber 400. In this case, the pressure-preserving push rod cabin and the valve cabin can be sequentially disassembled, and then the lower cylinder cover 60 is fixed on the lower end surface of the lower cylinder block 102, to finish pressure-preserving pushing of the entire lower piston rod 30, and implement pressure-preserving sealing of the lower cylinder block 102.

After the pressure-preserving conventional triaxial compression loading apparatus of the present invention has been assembled as above, the pressure-preserving conventional triaxial compression loading apparatus may be placed upright on a uniaxial tester to perform a pressure-preserving conventional triaxial loading test. During the test, the pressures of the hydraulic oil in the upper balance chamber 111, the lower balance chamber 151, and the annular inner chamber 410 of the annular oil bag 40 need to be separately adjusted according to specific test requirements. An air pressure in the upper compensation chamber 112 and the lower compensation chamber 152 may be adjusted according to specific test requirements, to compensate for the impact of the weight of a piston or assist in adjusting the magnitude of an axial load.

A method for completing a pressure-preserving conventional triaxial loading test of a fidelity specimen using the pressure-preserving conventional triaxial compression loading apparatus in the present invention is as follows:

The pressure-preserving conventional triaxial compression loading apparatus containing the fidelity specimen 7 is first placed upright on a uniaxial tester, then a hydrostatic pressure test, a deviatoric stress compression test, a free-end extrusion test, and a fixed-end extrusion test are separately performed on the fidelity specimen 7, the four kinds of tests are performed according to the need without sequence requirements, and specific methods of every test are separately as follows:

1. Hydrostatic Pressure Test

The annular inner chamber 410 of the annular oil bag 40 is in communication with hydraulic pipes of the upper balance chamber 111 and the lower balance chamber 151, and a hydrostatic pressure is synchronously applied to the fidelity specimen 7. In this case, no external load is applied to the upper and lower piston rods 20, 30, the air pressure in the upper compensation chamber 112 is increased to compensate for impact of the gravity of an upper piston, and the air pressure in the lower compensation chamber 152 is decreased to compensate for impact of the gravity of a lower piston. Axial and radial deformations of the fidelity specimen 7, an acoustic velocity change, and an acoustic emission event are measured in the test when the hydrostatic pressure changes. During the test, a pore pressure is capable of being servo controlled to remain unchanged, and a volume of a pore fluid flowing into or flowing out of the specimen chamber 400 is measured, or an inlet or outlet of the specimen chamber 400 is capable of being closed to measure a change in the pore pressure.

2. Deviatoric Stress Compression Test

The annular inner chamber 410 of the annular oil bag 40 is in communication with hydraulic pipes of the upper balance chamber 111 and the lower balance chamber 151, a hydrostatic pressure is synchronously applied to the fidelity specimen 7, and external load is applied to ends of the upper and lower piston rods 20, 30 to cause the upper and lower piston rods to actively move. Axial and radial deformations of the fidelity specimen 7, an acoustic velocity change, and an acoustic emission event are measured in different combinations of a hydrostatic pressure and a deviatoric stress. During the test, a pore pressure is capable of being servo controlled to remain unchanged, and a volume of a pore fluid flowing into or flowing out of the specimen chamber 400 is measured, or an inlet or outlet of the specimen chamber 400 is capable of being closed to measure a change in the pore pressure.

3. Free-End Extrusion Test

The upper balance chamber 111, the lower balance chamber 151, and the annular inner chamber 410 of the annular oil bag 40 are independent of each other and are not in communication, hydraulic pressures in the upper balance chamber 111 and the lower balance chamber 151 are servo controlled to be equal to a pore pressure of the specimen in the specimen chamber 400, axial movements of the piston rods are not limited, a hydraulic pressure in the annular inner chamber 410 of the annular oil bag 40 is increased, and an annular extrusion force is applied to the fidelity specimen 7.

Axial and radial deformations of the fidelity specimen 7, an acoustic velocity change, and an acoustic emission event are measured during extension under different extrusion forces. During the test, the pore pressure is capable of being servo controlled to remain unchanged, and a volume of a pore fluid flowing into or flowing out of the specimen chamber 400 is measured, or an inlet or outlet of the specimen chamber 400 is capable of being closed to measure a change in the pore pressure.

4. Fixed-End Extrusion Test

The upper balance chamber 111, the lower balance chamber 151, and the annular inner chamber 410 of the annular oil bag 40 are independent of each other and are not in communication. Hydraulic pressures in the upper balance chamber 111 and the lower balance chamber 151 are servo controlled to be equal to a pore pressure of the specimen in the specimen chamber 400, the piston rods are fixed, a hydraulic pressure in the annular inner chamber 410 of the annular oil bag 40 is increased, and an annular extrusion force is applied to the fidelity specimen 7. Axial and radial deformations of the fidelity specimen 7, an acoustic velocity change, and an acoustic emission event are measured under different extrusion forces when extension of the specimen is restricted. During the test, the pore pressure is capable of being servo controlled to remain unchanged, and a volume of a pore fluid flowing into or flowing out of the specimen chamber 400 is measured, or an inlet or outlet of the specimen chamber 400 is capable of being closed to measure a change in the pore pressure.

The pressure-preserving conventional triaxial compression loading apparatus in the present invention is used to perform the foregoing conventional triaxial loading test on a fidelity specimen, so that the test data of the fidelity specimen can be obtained more accurately, to help to study the mechanical behavior of rock and measure their mechanical properties more faithfully.

The pressure-preserving conventional triaxial compression loading apparatus in the present invention may be further configured to perform a conventional triaxial loading test on a traditional rock specimen. The traditional rock specimen is manually put into the specimen chamber from the lower port of the lower cylinder block, and then a lower piston rod assembly, a lower sealing assembly, and a lower cylinder cover assembly are mounted. After mounting is completed, the pressure-preserving conventional triaxial compression loading apparatus in the present invention containing the traditional rock specimen is placed on an existing uniaxial tester to perform a conventional triaxial loading test, so that the existing uniaxial tester is upgraded to a conventional triaxial tester.

Compared with the prior art, the pressure-preserving conventional triaxial compression loading apparatus in the present invention can more conveniently implement a hydrostatic pressure test, and can also perform an extrusion test, thereby meeting the requirements of conventional triaxial loading tests of various types of rock.

Compared with the prior art, the pressure-preserving conventional triaxial compression loading apparatus in the present invention has the following beneficial effects: The specimen chamber defined by the upper piston rod, the lower piston rod, and the inner wall of the annular oil bag accommodates a fidelity specimen. The pressure in the upper and lower balance chambers, the annular inner chamber of the annular oil bag, and the specimen chamber are set respectively to preserve pore pressure of the fidelity specimen, to ensure a pressure-preserving state of the fidelity specimen. The annular oil bag and the upper and lower piston rods are used to apply additional loading, to implement a pressure-preserving conventional triaxial loading test of the fidelity specimen. A variety of measuring sensors disposed in the annular inner chamber of the annular oil bag are used to obtain the test data when performing the conventional triaxial loading test on the fidelity specimen. Therefore, it resolve the problem that a triaxial tester in the prior art cannot perform pressure-preserving loading and testing on a fidelity specimen, so that the test data is more accurate and reliable, to help to study the mechanical behavior of in-situ rock and measure their mechanical properties more faithfully. In addition, the pressure-preserving conventional triaxial compression loading apparatus of the present invention is easily portable and more convenient to use, and can be used in combination with a common uniaxial tester, thereby greatly reducing test costs.

The foregoing embodiments are merely descriptions of preferred implementations of the present invention and are not used to limit the scope of the present invention. Various variations and improvements made by a person of ordinary skill in the art to the technical solutions of the present invention without departing from the design spirit of the present invention shall fall within the protection scope determined by the claims of the present invention.

INDUSTRIAL APPLICABILITY

The pressure-preserving conventional triaxial compression loading apparatus of the present invention can accommodate a fidelity specimen, and can implement a pressure-preserving conventional triaxial loading test of the fidelity specimen, so that the test data is more accurate and reliable, to help to study the mechanical behavior of in-situ rock and measure their mechanical properties more faithfully.

The invention claimed is:

1. A pressure-preserving conventional triaxial compression loading apparatus, comprising: a pressure vessel, an upper piston rod, a lower piston rod, and an annular oil bag assembly, wherein the pressure vessel is formed by connecting an upper cylinder block and a lower cylinder block using bolts in a sealed manner, an upper annular boss is disposed on the upper piston rod, an annular area of the upper annular boss is equal to a cross-sectional area of the upper piston rod, a lower annular boss is disposed on the lower piston rod, an annular area of the lower annular boss is equal to a cross-sectional area of the lower piston rod, hollow chambers of the pressure vessel in vertical communication sequentially comprise an upper chamber, an upper sealed chamber, a confining pressure chamber, a lower sealed chamber, and a lower chamber from top to bottom, an upper cylinder cover is fixedly sealed on an upper end surface of the pressure vessel, the upper annular boss fits the upper chamber in a sealed manner, the upper piston rod located below the upper annular boss fits the upper sealed chamber in a sealed manner, the upper piston rod located above the upper annular boss passes upward through the upper cylinder cover to fit the upper cylinder cover in a sealed manner, the upper annular boss of the upper piston rod divides the upper chamber into two chambers independent of each other, the two chambers are an upper balance chamber located above the upper annular boss and an upper compensation chamber located below the upper annular boss, a lower port of the lower chamber of the pressure vessel is provided with a lower sealing assembly fitting the lower port in a sealed manner, a lower cylinder cover is fixed on a lower end surface of the pressure vessel, the lower piston rod located above the lower annular boss fits the lower sealed chamber in a sealed manner, the lower annular boss fits the lower chamber in a sealed manner, the lower piston rod located below the lower annular boss sequentially passes downward through an inner hole of the lower sealing assembly and the lower cylinder cover, the lower piston rod fits the inner hole of the lower sealing assembly in a sealed manner, the lower annular boss of the lower piston rod divides the lower chamber into two chambers independent of each other, the two chambers are a lower balance chamber located below the lower annular boss and a lower compensation chamber located above the lower annular boss, the annular oil bag assembly is placed in the confining pressure chamber, the annular oil bag assembly comprises an oil bag support and an annular oil bag fixed in the oil bag support, the oil bag support is inserted in a concave groove that is in an inner wall of the confining pressure chamber and fits the oil bag support, when an annular inner chamber of the annular oil bag is filled with medium, an outer wall of the annular oil bag and the inner wall of the confining pressure chamber are attached together, a fidelity specimen is placed in a specimen chamber defined by a lower end surface of the upper piston rod, an upper end surface of the lower piston rod, and an inner wall of the annular oil bag, a variety of measuring sensors are disposed in the annular inner chamber of the annular oil bag, and the annular inner chamber, the specimen chamber, the upper balance chamber, the upper compensation chamber, the lower balance chamber, and the lower compensation chamber are chambers independent of each other and are separately provided with independent inlet and outlet pipes.

2. The pressure-preserving conventional triaxial compression loading apparatus according to claim 1, wherein the oil bag support comprises an upper annular body, a lower annular body, and several connecting rods, each connecting rod is a C-shaped body protruding outward, an upper end of the connecting rod is connected to an outer side surface of the upper annular body, a lower end of the connecting rod is connected to an outer side surface of the lower annular body, the upper annular body, the lower annular body, and the connecting rods are separately inserted in concave grooves that are in the inner wall of the confining pressure chamber and respectively fit the upper annular body, the lower annular body, and the connecting rods, end surfaces and inner side surfaces of the upper annular body and the lower annular body fit the concave grooves in the inner wall of the confining pressure chamber in a sealed manner, and the outer side surfaces of the upper annular body and the lower annular body and outer side surfaces of the connecting rods are provided with concave grooves for arranging a wire.

3. The pressure-preserving conventional triaxial compression loading apparatus according to claim 2, wherein an upper limit assembly of the upper piston rod is disposed on an upper end surface of the upper cylinder cover, and a lower limit assembly of the lower piston rod is disposed on a lower end surface of the lower cylinder cover.

4. The pressure-preserving conventional triaxial compression loading apparatus according to claim 3, wherein an upper load sensor and an upper displacement meter for measuring the upper piston rod are further disposed on the upper end surface of the upper cylinder cover, and a lower load sensor and a lower displacement meter for measuring the lower piston rod are disposed on the lower end surface of the lower cylinder cover.

5. The pressure-preserving conventional triaxial compression loading apparatus according to claim 2, wherein the measuring sensors include a radial displacement sensor, an acoustic emission detector, and a thermometer, and a heating rod or a cooling rod is further disposed in the oil bag support.

6. The pressure-preserving conventional triaxial compression loading apparatus according to claim 5, wherein an upper platen assembly is disposed on the lower end surface of the upper piston rod, a lower platen assembly is disposed on the upper end surface of the lower piston rod, the upper platen assembly and the lower platen assembly have the same structure, each of the upper platen assembly and the lower platen assembly comprises a platen fixed on an end surface of a piston rod and a transverse wave velocity probe, a longitudinal wave velocity probe, and an acoustic emission probe that are mounted on the platen and are in contact with the fidelity specimen, through holes in communication with the platens of the upper and lower platen assemblies are respectively provided at axes of the upper and lower piston rods, a measurement apparatus measuring an axial displacement is capable of being placed in each through hole, and the platens of the upper and lower platen assemblies respectively fit the through holes at the axes of the upper and lower piston rods in a sealed manner.

7. The pressure-preserving conventional triaxial compression loading apparatus according to claim 6, wherein a thermal insulation lining is disposed on the outer wall of the annular oil bag, and is used for attenuating heat transfer between the annular inner chamber of the annular oil bag and the oil bag support and the inner wall of the confining pressure chamber.

8. The pressure-preserving conventional triaxial compression loading apparatus according to claim 1, wherein the lower sealing assembly-comprises a rotary seal ring and a positioning clamping ring, a plurality of limiting blocks protruding inward are arranged at intervals in a circumferential direction on an inner side surface of a lower port of the lower cylinder block, clamping blocks corresponding to the limiting blocks are disposed in a circumferential direction on an outer side surface of a lower end of the rotary seal ring, the clamping blocks of the rotary seal ring are separately inserted into clamping grooves between the limiting blocks of the lower cylinder block from the lower end, continue to move upward to be above the limiting blocks, and rotate to clamp the clamping blocks between upper end surfaces of the limiting blocks and a hole shoulder in the lower chamber, an inner side surface of the rotary seal ring fits the lower piston rod in a sealed manner, an outer side surface of an upper end of the rotary seal ring fits an inner wall of the lower chamber in a sealed manner, positioning blocks that protrude outward and correspond to the clamping grooves between the limiting blocks are disposed in a circumferential direction on an outer side surface of the positioning clamping ring, upper end surfaces of the positioning blocks are higher than an upper end surface of the positioning clamping ring, and after the positioning blocks are inserted in the clamping grooves between the limiting blocks and clamping grooves between the clamping blocks, the upper end surface of the positioning clamping ring fits a lower end surface of the rotary seal ring, and a lower end surface of the positioning clamping ring is flush with a lower end surface of the lower cylinder block.

9. A method for performing a pressure-preserving conventional triaxial loading test on a fidelity specimen using the pressure-preserving conventional triaxial compression loading apparatus according to claim 8, wherein the pressure-preserving conventional triaxial compression loading apparatus containing the fidelity specimen is first placed upright on a uniaxial tester, then a hydrostatic pressure test, a deviatoric stress compression test, a free-end extrusion test, and a fixed-end extrusion test are separately performed on the fidelity specimen, the four kinds of tests are performed according to the need without sequence requirements, and specific methods of every test are separately as follows:

a. in the hydrostatic pressure test, the annular inner chamber of the annular oil bag is in communication with hydraulic pipes of the upper balance chamber and the lower balance chamber, and a hydrostatic pressure is synchronously applied to the fidelity specimen; in this case, no external load is applied to the upper and lower piston rods, the air pressure in the upper compensation chamber is increased to compensate for impact of the gravity of an upper piston, and the air pressure in the lower compensation chamber is decreased to compensate for impact of the gravity of a lower piston; axial and radial deformations of the fidelity specimen, an acoustic velocity change, and an acoustic emission event are measured in the test when the hydrostatic pressure changes; and during the test, a pore pressure is capable of being servo controlled to remain unchanged, and a volume of a pore fluid flowing into or flowing out of the specimen chamber is measured, or an inlet or outlet of the specimen chamber is capable of being closed to measure a change in the pore pressure;

b. in the deviatoric stress compression test, the annular inner chamber of the annular oil bag is in communication with hydraulic pipes of the upper balance chamber and the lower balance chamber, a hydrostatic pressure is synchronously applied to the fidelity specimen, and external load is applied to ends of the upper and lower piston rods to cause the upper and lower piston rods to actively move; axial and radial deformations of the fidelity specimen, an acoustic velocity change, and an acoustic emission event are measured in different combinations of a hydrostatic pressure and a deviatoric stress; and during the test, a pore pressure is capable of being servo controlled to remain unchanged, and a volume of a pore fluid flowing into or flowing out of the specimen chamber is measured, or an inlet or outlet of the specimen chamber is capable of being closed to measure a change in the pore pressure;

c. in the free-end extrusion test, hydraulic pipes of the upper balance chamber, the lower balance chamber, and the annular inner chamber of the annular oil bag are independent of each other and are not in communication, hydraulic pressures in the upper balance chamber and the lower balance chamber are servo controlled to be equal to a pore pressure of the specimen in the specimen chamber, axial movements of the piston rods are not limited, a hydraulic pressure in the annular inner chamber of the annular oil bag is increased, and an annular extrusion force is applied to the fidelity specimen; axial and radial deformations of the fidelity specimen, an acoustic velocity change, and an acoustic emission event are measured during extension under different extrusion forces; and during the test, the pore pressure is capable of being servo controlled to remain unchanged, and a volume of a pore fluid flowing into or flowing out of the specimen chamber is measured, or an inlet or outlet of the specimen chamber is capable of being closed to measure a change in the pore pressure; and d. in the fixed-end extrusion test, hydraulic pipes of the upper balance chamber, the lower balance chamber, and the annular inner chamber of the annular oil bag are independent of each other and are not in communication, hydraulic pressures in the upper balance chamber and the lower balance chamber are servo controlled to be equal to a pore pressure of the specimen in the specimen chamber, the piston rods are fixed, a hydraulic pressure in the annular inner chamber of the annular oil bag is increased, and an annular extrusion force is applied to the fidelity specimen; axial and radial deformations of the fidelity specimen, an acoustic velocity change, and an acoustic emission event are measured under different extrusion forces when extension of the fidelity specimen is restricted; and during the test, the pore pressure is capable of being servo controlled to remain unchanged, and a volume of a pore fluid flowing into or flowing out of the specimen chamber is measured, or an inlet or outlet of the specimen chamber is capable of being closed to measure a change in the pore pressure.

* * * * *